United States Patent [19]

Isaacs et al.

[11] Patent Number: 5,624,958
[45] Date of Patent: *Apr. 29, 1997

[54] DISINFECTING CONTACT LENSES

[76] Inventors: Charles E. Isaacs, 30 Devon Dr. North, Manalapan, N.J. 07726; Kwang S. Kim, 178 Dahlia St., Staten Island, N.Y. 10312; Halldor Thormar, Langagerdi 15, Reykjavik, Iceland; William C. Heird, 2001 Holcombe Blvd. Apt. 2701, Houston, Tex. 77030; Henryk M. Wisniewski, 141 Nixon Ave., Staten Island, N.Y. 10304

[*] Notice: The term of this patent shall not extend beyond the expiration date of Pat. No. 5,434,182.

[21] Appl. No.: 408,079

[22] Filed: Mar. 22, 1995

Related U.S. Application Data

[63] Continuation-in-part of Ser. No. 58,056, May 3, 1993, Pat. No. 5,434,182, which is a continuation of Ser. No. 896,120, Jun. 10, 1992, abandoned, which is a continuation-in-part of Ser. No. 543,111, Jun. 25, 1990, abandoned, which is a continuation-in-part of Ser. No. 365,291, Jun. 12, 1989, abandoned, which is a continuation-in-part of Ser. No. 140,078, Dec. 31, 1987, Pat. No. 4,997,851.

[51] Int. Cl.$^6$ .................. A61K 31/22; A61K 31/225; A61K 31/20
[52] U.S. Cl. .............. 514/546; 514/547; 514/549; 514/552; 514/557; 514/558
[58] Field of Search .................. 514/546, 547, 514/549, 552, 557, 558

[56] References Cited

U.S. PATENT DOCUMENTS

| | | | |
|---|---|---|---|
| 4,223,041 | 9/1980 | Carroll | 424/322 |
| 4,489,079 | 12/1984 | Stone | 514/557 |
| 4,513,008 | 4/1985 | Revici et al. | 514/703 |

*Primary Examiner*—Zohreh Fay
*Attorney, Agent, or Firm*—Kane, Dalsimer, Sullivan, Kurucz, Levy, Eisele and Richard

[57] ABSTRACT

A process of disinfecting a contact lens entails applying to the lens a mixture solution of an effective antimicrobial amount of a fatty acid, monoglyceride thereof or ether or lysophosphatidylcholine derivatives thereof.

12 Claims, No Drawings

DISINFECTING CONTACT LENSES

CROSS-REFERENCE TO RELATED APPLICATIONS

This application is a continuation-in-part of U.S. patent application Ser. No. 08/058,056, filed May 3, 1993, now U.S. Pat. No. 5,434,182, as a continuation of U.S. application Ser. No. 07/896,120 filed Jun. 10, 1992, now abandoned, and which was a continuation-in-part of U.S. patent application Ser. No. 543,111, filed Jun. 25, 1990, now abandoned, which is a continuation-in-part of U.S. patent application Ser. No. 365,291, filed Jun. 12, 1989, now abandoned, which is a continuation-in-part of U.S. patent application Ser. No. 140,078, filed Dec. 31, 1987, now U.S. Pat. No. 4,997,851.

BACKGROUND OF THE INVENTION

1. Field of the Invention

The invention relates to contact lenses and more particularly to methods and compositions for disinfecting such lenses.

2. Brief Description of Related Art

Anti-microbials used in disinfecting ocular prostheses such as contact lenses or employed to preserve ophthalmic formulations designed to be applied directly to the eye or to objects which are in direct contact with the eyes, must be non-irritating and free of any detrimental side effects. Moreover, they must be sufficiently effective against bacteria, viruses and fungi to ensure the sterility of the prostheses or guarantee a reasonable shelf-life of the ophthalmic formulations and thereby prevent infections. The inherent conflict between antimicrobial efficiency on the one hand, and non-irritancy on the other has lead to compromises. The known anti-microbial agents which are found in ophthalmic formulations include:

Benzalkonium chloride, benzethonium chloride, benzyl alcohol, chlorobutanol, chlorhexidine digluconate or diacetate, methyl and propyl hydroxybenzoate(parabens), phenylethyl alcohol, phenylmercuric acetate or nitrate, sorbic acid, thimerosal, alpha-4[1-tris(2-hydroxyethyl) ammonium chloride-2-dibutenyl]poly(1-dimethyl ammonium chloride-2-dibutenyl]-ω-tris (2-hydroxyethyl) ammonium chloride, and poly[aminopropyl bis(biguanide)]or poly[hexamethylene-bis(biguanide].

Some attributes of a disinfectant/preservative, which would be very desirable from an ophthalmic point of view, are:

1) Bactericidal and fungicidal activity at concentration levels which are much lower than those likely to cause damage to mammalian cells, i.e. selective toxicity.
2) Nonirritant to the ocular surface upon topical application.
3) Innocuous toward corneal epithelial or endothelial cells.
4) Effective in the physiological Ph range, i.e. Ph 6–8.
5) Not acting as a sensitizing agent to ocular tissues (unlike thimerosal and chlorhexidine).
6) Readily compatible in aqueous solution.
7) Chemically and thermally stable in aqueous media and able to withstand radiation sterilization.
8) Possessing prolonged chemical stability in aqueous mixtures at physiological pH's (acceptable shelf-life).
9) Not absorbed into the polymer matrix of hydrogel lenses thereby not accumulating within the matrix of the lens nor leaching into the ocular tissues upon application of the lens to the eye.
10) Not adsorbed adversely onto the surface of the contact lenses, so as to diminish the water wettability of such lenses, nor increases the water/lens interfacial tension appreciably and thereby reduce lens ocular compatibility and perceived in-eye comfort.
11) Not interfering with the solubility or other properties of the components of the ocular formulation to be preserved such as contact lens wetting, film forming, and viscosity-modifying agents or therapeutic agents.
12) Neither absorbed into nor adsorbed onto the polymers used in the construction of eye-dropper containers (bottles).
13) Not absorbed systemically, i.e. by the bodily organs via the circulatory system.
14) Free of toxic heavy metal ions which may act as cumulative poisons in the body.

It is important to note here that none of the earlier listed presently known preservatives fulfill all of the above criteria especially those listed as items 9 and 10.

Until recently, virtually all of the commercially available hydrogel lenses were fabricated from neutral polymeric materials such as poly(HEMA). However, the introduction of disposable lenses, such as those sold under the brand name "Acuvue" by Johnson and Johnson, Inc., has led to the reintroduction and widespread use of a contact lens material fabricated by the anionic Etafilcon A® and containing methylmethacrylic acid groups. Such lenses are not ideally suited for use with ophthalmic solutions containing polyquaternary ammonium antimicrobial agents, since the latter agents react electrostatically with the surfaces of such materials.

Clinical impressions suggest that such polyquaternary ammonium disinfectant solutions do indeed adsorb to the surfaces of certain soft lens materials, especially anionic materials, and cause ocular discomfort. It is essential for the lens to retain its wettability and low interfacial tension against tear, and allow a continuous film of tear fluid covering, in order to remain acceptable to the contact lens wearer.

While there may be many industrial and even pharmaceutical disinfectants and preservatives available, their suitability to ophthalmic applications is never obvious and their potential must be first recognized, then carefully formulated and clinically tested to achieve a satisfactory balance of efficacy, safety and contact lens compatibility.

The present invention provides a means of disinfecting a contact lens with an agent which satisfies the 12 attributes listed above as desirable for the anti-microbial agent.

SUMMARY OF THE INVENTION

The invention comprises a process for disinfecting a contact lens, which comprises; applying to the lens an effective antimicrobial amount of a compound selected from the group consisting of $C_6$–$C_{14}$ fatty acids and monoglycerides thereof, $C_6$–$C_{14}$ fatty alcohols (ether linkages), $C_{16}$–$C_{20}$ mono-or polyunsaturated fatty acids and monoglycerides thereof, $C_{16}$–$C_{20}$ mono- or polyunsaturated fatty alcohols, and ether and lysophosphatidylcholine derivatives of $C_4$–$C_{22}$ fatty acids.

The process of the invention disinfects contact lenses through the anti-microbial, anti-viral activity of the selected compound in an aqueous carrier. The application can be by immersion, i.e., "soaking" in the carrier. The process can also affect anti-microbial activity on the surface of the eye.

DETAILED DESCRIPTION OF THE PREFERRED EMBODIMENTS OF THE INVENTION

Hydrophilic or partially hydrophilic plastic materials have been described for use in making so called "soft contact lenses". For example, U.S. Pat. No. 3,503,393 to Seiderman and U.S. Pat. No. 2,976,576 to Wichterle describe processes for producing three dimensional hydrophilic polymers of polyhydroxyethylmethacrylate in aqueous reaction media having a sparingly cross-linked polymeric hydrogel structure and having the appearance of elastic, soft, transparent hydrogels. Other soft contact lenses include lenses made out of silicone and other optically suitable flexible materials.

The process of the present invention is useful to disinfect the known soft contact lenses described above, and others, for example as described in the U.S. Pat. Nos. 4,931,279; 4,045,547; and 4,056,496. In a particular embodiment of the invention, the process of the: invention can also be carried out in a continuous manner by incorporating the anti-microbial compositions described herein, into the self-medicating contact lenses, such as described for example in the U.S. Pat. Nos. 3,786,812 and 4,571,039.

The main virtues of these lenses is their softness and optical lens suitability. The hydrophilic lenses are particularly useful in ophthalmology due to their remarkable ability to absorb water with a concomitant swelling to a soft mass of extremely good mechanical strength, complete transparency and the ability to retain shape and dimensions when equilibrated in a given fluid.

One of the problems connected with these soft contact lenses is the method of their cleaning. The very property of the hydrophilic soft lenses which allows them to absorb up to 150 percent by weight of water also allows formulations which might otherwise be used for cleaning to be absorbed and even concentrated and later released when the soft contact lens is on the eye. The release may be much slower than the uptake; therefore the cleaner continues to build-up in the lenses. This build-up eventually affects the physical characteristics of the lenses including dimension, color, etc. This can have the harmful result of damaging or staining the contact lens itself and/or harming the sensitive tissues of the conjunctivae or cornea.

The anti-microbial compounds described above and employed in the process of the invention exhibit varying degrees of anti-viral activity. Representative of this activity is that listed as shown in the following Table 1.

TABLE 1

Viral inactivation by incubation with fatty acids at 37° for 30 min.

| Fatty Acid | Concn[a] in mg/ml (Mm) | Reduction of virus titer ($\log_{10}$) | | |
|---|---|---|---|---|
| | | VSV | HSV-1 | VV[b] |
| Butyric (4:0)[c] | 10 (113) | 0 | ND[d] | ND |
| Caproic (6:0) | 10 (86) | 0 | ND | ND |
| Caprylic (8:0) | 10 (69) | 1.8 | ND | ≧3.2 |
| Capric (10:0) | 4 (22) | ≧4.0[e] | ≧4.0 | ≧3.2 |
| Lauric (12:0) | 2 (10) | ≧4.0 | ≧4.0 | ≧3.2 |
| Myristic (14:0) | 4 (16) | ≧4.0 | ≧4.0 | 1.7 |
| Palmitic (16:0) | 20 (78) | 1.0 | 1.0 | .7 |
| Palmitoleic (16:1) | 2 (15) | ≧4.0 | ≧4.0 | ≧3.2 |
| Stearic (18:0) | 20 (70) | 0 | ND | |
| oleic (18:1 cis) | 2 (7) | ≧4.0 | ≧4.0 | ≧3.2 |
| Elaidic (18:1 trans) | 2 (7) | ≧4.0 | ≧4.0 | |
| Linoleic (18:2) | 1 (3.5) | ≧4.0 | ≧4.0 | ≧3.2 |
| Linolenic (18:3) | 1 (3.6) | ≧4.0 | ≧4.0 | ≧3.2 |
| Arachidonic (20:4) | 0.5 (1.6) | ≧4.0 | ND | |

TABLE 1-continued

Viral inactivation by incubation with fatty acids at 37° for 30 min.

| Fatty Acid | Concn[a] in mg/ml (Mm) | Reduction of virus titer ($\log_{10}$) | | |
|---|---|---|---|---|
| | | VSV | HSV-1 | VV[b] |

[a]Concentration of fatty acid in virus mixtures incubated at 37° C. for 30 min. All fatty acids were tested in a series of twofold concentrations. Shown is either the lowest concentration which reduced the VSV titer by ≧4.0 $\log_{10}$ units of the highest concentration tested (butyric, caproic, caprylic, palmitic, and stearic).
[b]VV, Visna virus.
[c]Carbon atoms: double bonds.
[d]ND, Not done.
[e]The titer ($\log_{10}$) of the control virus incubated with mm was 5.5, whereas no virus was detectable in the $10^{-2}$ to $10^{-5}$ dilutions of fatty acid-virus mixtures. It was not possible to test these mixtures in lower dilutions ($10^{-1}$ or undiluted) because they were toxic to the cell cultures. Assuming that the $10^{-1}$ dilution contained infectious virus, the highest possible titer of the fatty acid-virus mixture was $10^{1.5}$ TCID$_{50}$, and the reduction of virus titer ($\log_{10}$) would equal 4.0 (5.5 minus 1.5). If the titers of the mixtures were less than $10^{1.5}$, the reduction of titer would be greater than 4.0.

It can be seen from Table 1, above, that short-chain (butyric, caproic, and caprylic) and long-chain saturated (palmitic and stearic) fatty acids had no or a very small antiviral effect at the highest concentrations tested. On the other hand, the medium-chain saturated and long-chain unsaturated fatty acids were all antiviral but at different concentrations. Table 1 also shows the lowest concentration causing a 10,000-fold reduction in VSV titer. A 2-fold-lower concentration either did not inactivate the virus or caused only a 10-fold reduction in titer. Similar results were obtained for HSV-1 and visna virus, a retrovirus. In contrast, incubation of poliovirus at 37° C. for 30 min. with capric, lauric, myristic, palmitoleic, oleic, linoleic, linolenic, and arachidonic acids, each at a concentration of 8 mg/ml, did not cause a significant reduction of virus titer compared with the titer of poliovirus incubated without fatty acids ($10^{4.7}$ TCID$_{50}$). The sodium salts of oleic and linoleic acids had anti-viral effects similar to those of the free acids.

Other products of lipolysis, e.g., 1-monoglycerides of fatty acids, were also tested for antiviral activity, as shown in the following Table 2:

TABLE 2

Viral inactivation in human serum by incubation with monoglycerides at 37° C. for 30 min

| Monoglyceride | Concn[a] in mg/ml (Mm) | Reduction of virus titer ($\log_{10}$) | |
|---|---|---|---|
| | | VSV | HSV-1 |
| Monocaprylin (8:0)[b] | 2.0 (9) | ≧4.0 | ND[c] |
| Monocaprin (10:0) | 0.5 (2) | ≧4.0 | ≧3.7 |
| Monolaurin (12:0) | 0.25 (0.9) | ≧4.0 | ≧3.7 |
| Monomyristin (14:0) | 2.0 (13) | 3.0 | ND |
| Monoolein (18:1) | 1.0 (2.8[d]) | 2.3 | ND |
| Monolinolein (18:2) | 0.25 (0.7) | ≧4.0 | ND |

[a]Lowest concentration causing ≧3.0 $\log_{10}$ reduction in virus titer.
[b]Carbon atoms: double bonds.
[c]ND, Not done.
[d]Highest antiviral activity of the concentrations tested (0.5 to 4 mg/ml). The same results were obtained when the monoglyceride was dissolved in ethanol and diluted 1:100 in mm before being added to the virus.

All the monoglycerides tested except monomyristin and monoolein were antiviral in concentrations 5 to 10 times lower (millimolar) than those of the corresponding fatty acids.

The above experiments show that the monoglycerides and fatty acids tested kill enveloped viruses.

Studies have also been done to determine the time required for viral inactivation. Virus was incubated with monolaurin (12:0) in maintenance media. The results are shown below in Table 3.

TABLE 3

Time Course of Viral Inactivation

| Incubation Time (min) | Reduction of HSV-1 titer |
| --- | --- |
| 30 | ≧4.0 |
| 10 | ≧4.0 |
| 5 | ≧4.0 |
| 1 | ≧4.0 |
| 0.5 | ≧4.0 |

These results indicate that viral killing is rapid and probably happens as the monoglyceride or fatty acid comes into contact with the viral envelope. Electron micrographs with negative staining of VSV incubated with linoleic acid showed that at 0.5 mg per ml leakage of viral envelopes was produced allowing the stain to enter many particles. The effect was far more pronounced with 1 mg of linoleic acid per ml, causing particle disintegration.

Effect of fatty acids on viral particles.

To study the effect of fatty acids on virus particles, VSV was concentrated, partly purified, and then incubated at 37° C. for 30 min in maintenance medium with or without linoleic acid. Negative staining of virus incubated without fatty acids showed an abundance of characteristic bullet-shaped particles covered with spikes and containing coiled nucleocapsids (see FIG. 1a of U.S. Pat. No. 4,997,851, incorporated herein by reference). Incubation with 0.5 mg of linoleic acid per ml caused leakage of viral envelopes, allowing the stain to enter many particles (see FIG. 1b of U.S. Pat. No. 4,997,851, incorporated herein by reference). The effect was far more pronounced with 1 mg of linoleic acid per ml (see Fig. 1c of U.S. Pat. No. 4,997,851, incorporated herein by reference), causing particle disintegration. Titration of the samples used for electron microscopy showed a 10-fold reduction in virus titer with 0.5 mg of linoleic acid per ml, whereas 1 mg/ml caused a ≧1,000-fold reduction. Similar results were obtained by negative staining of VSV incubated with low concentrations of arachidonic acid.

Disintegration of cell membranes by fatty acid.

Negative staining of VSV treated with fatty acids suggested that virus inactivation results from disruption of the viral envelope, which is derived from the host cell plasma membrane. To study the effect on cell membranes, monolayers of Vero cells or sheep fibroblasts were incubated at 37° C. for 30 min. in maintenance medium (MM) with or without 1 mg of linoleic acid per ml and examined by scanning electron microscopy. Control cells incubated in maintenance medium (MM) without fatty acids showed intact cell membranes (see FIG. 2c of U.S. Pat. No. 4,997,851, incorporated herein by reference), whereas in cell layers treated with 1 mg of linoleic acid per ml, the cell membranes were partly or completely disintegrated (see FIG. 2d of U.S. Pat. No. 4,997,851, incorporated herein by reference), causing cell lysis.

Micrographs of VSV particles show the effect of linoleic acid treatment. Titration of the samples used for electron microscopy show a ≦10-fold reduction in virus titer with 0.5 mg of linoleic acid per ml whereas 1 mg/ml caused a ≧10,000-fold reduction. Similar results were obtained by negative staining of VSV incubated with low concentrations of arachidonic acid.

It was next examined whether the effects of antiviral fatty acids were additive so that changes in the concentration of one antiviral component in a mixture can be compensated for by increasing or adding another fatty acid. Mixtures of fatty acids were made in which individual fatty acid concentrations had been found to either not inactivate the virus, or to reduce the titer by less than 10-fold. Mixtures were incubated with virus in maintenance medium. The results are set forth in the following Table 4.

TABLE 4

Antiviral Activity of Fatty Acid Mixtures

| Fatty Acid Mixture | Individual Fatty Acid Conc. (mg/ml) | Total Fatty Acid Conc. (mg/ml) | Reduction of VSV titer ($\log_{10}$) |
| --- | --- | --- | --- |
| Capric | 2 | 3 | ≧3.7 |
| Lauric | 1 | | |
| Lauric | 1 | 2 | ≧3.7 |
| Myristic | 1 | | |
| Lauric | 1 | 2 | ≧3.7 |
| Oleic | 1 | | |
| Oleic | 1 | .5 | ≧3.7 |
| Linoleic | 0.5 | | |
| Lauric | 0.7 | | |
| Oleic | 0.7 | 1.7 | ≧3.7 |
| Linoleic | 0.3 | | |

The ability to make antiviral mixtures of medium and long-chain fatty acids indicates that a balance can be made between the potentially toxic effects of high concentrations of medium chain fatty acids in vivo and the loss of antiviral long-chain fatty acids by binding to serum albumin and other blood proteins.

Effect of an Antiviral Monoglyceride on CMV Titers.

Monocaprin (10:0), which had previously been found to inactivate HSV-1 at a concentration of 2 Mm, was tested against three separate CMV strains. Incubations were performed in a maintenance medium containing 10% serum. The results are set forth in the following Table 5.

TABLE 5

Inactivation of CMV by a Purified Lipid

| CMV Strain Tested | Reduction of CMV Titer ($\log_{10}$ TCID 50%)* |
| --- | --- |
| AD 169 | ≧3.69 |
| Espilat | ≧3.50 |
| Towne | ≧2.67 |

*TCID 50% - Tissue culture infective dose 50%, expressed as $\log_{10}$.

The above results establish that CMV as well as HSV-1, HIV, and other enveloped viruses can be inactivated by the anti-microbials described herein.

Monoglyceride Inactivation of HSV-1 in Human Serum.

HSV-1 was added directly to human serum, and virus inactivation was measured in the presence of either monocaprin (10:0) or monolaurin (12:0). The results are set forth in the following Table 6.

TABLE 6

HSV-1 Inactivation in Human Serum

| Monoglyceride Added* | Conc. (mg/ml) | Reduction in HSV-1 titer ($\log_{10}$) |
|---|---|---|
| Control | — | 0 |
| Monocaprin | 1 | 0.8 |
| Monocaprin | 2 | 1.8 |
| Monocaprin | 4 | ≧4.0 |
| Monolaurin | 1 | 0.8 |
| Monolaurin | 2 | 1.5 |
| Monolaurin | 4 | 2.0 |

*The incubation mixture contained human serum, HSV-1 (titer 5.5), and the indicated monoglyceride.

Monolaurin at 4 mg/ml reduced serum HSV-1 titer by only 100-fold whereas monocaprin at the same concentration decreased the viral titer by ≧10,000-fold. In our in vitro studies, monolaurin had more antiviral activity on a concentration basis (millimolar) than monocaprin.

Fatty acids and monoglycerides are antibacterial as well as antiviral; see the U.S. Pat. No. 4,997,851 which is hereby incorporated herein by reference thereto. Included within bacterial species susceptible to inactivation by these compounds are Staphylococcus epidermidis (gram +), Escherichia coli (gram −), Salmonella enteritidis (gram −) and Pseudomonas aeruginosa.

Gram positive bacteria were inactivated comparably by medium chain saturated and long-chain unsaturated monoglycerides. However, the gram − bacteria E. coli and S. enteritidis were unaffected by long-chain unsaturated fatty acids and monolaurin. H. influenzae was inactivated by monolaurin so that there are differential sensitivities to monoglycerides between different gram negative bacteria. Differences in bacterial inactivation may be due to the bacterial wall, membrane or both. Scanning electron micrographs of S. epidermidis treated with monolaurin showed that the bacteria were completely disintegrated. It is therefore possible to manipulate monoglycerides of fatty acids and their concentrations to lyse some membranes and leave others intact.

The compounds used in the present invention may be selected from the group consisting of saturated or unsaturated fatty acids having from 4 to 22 carbon atoms, esters or ethers of glycerol with said acids, and saturated or unsaturated fatty alcohols having from 4 to 22 carbon atoms, especially from 6 to 14 carbon atoms. Preferred compounds comprise saturated fatty acids having from 4 to 14 carbon atoms, particularly from 6 to 14 carbon atoms, and monoglycerides thereof, and saturated fatty alcohols having from 6 to 14 carbon atoms. Especially preferred are $C_7$–$C_{12}$ fatty acid monoglycerides, either singly or in mixtures thereof. Also useful according to the invention are mono- or polyunsaturated fatty acids having from 14 to 22 carbon atoms, especially from 16 to 20 or from 16 to 18 carbon atoms, and the monoglycerides thereof, and mono- or polyunsaturated fatty alcohols having from 14 to 22 or 16 to 20 carbon atoms. The above-mentioned ranges of carbon atoms are inclusive of fatty acids having odd numbered carbon atoms.

It is also within the scope of the invention to employ ether and/or lysophosphatidylcholine derivatives of $C_4$–$C_{22}$ fatty acids having antimicrobial, especially antiviral and/or antibacterial, activity. For example, useful fatty acid derivatives would have an ether bond between a fatty acid and glycerol. Examples of such compounds include 1-O-decyl-sn-glycerol, 1-O-lauryl-sn-glycerol, 1-O-octyl-sn-glycerol, and 1-O-oleyl-sn-glycerol. Useful lysophosphatidylcholine derivatives include, for example, L-α-lysophosphatidylcholine caproyl, L-α-lysophosphatidylcholine decanoyl, and L-α-lysophosphatidycholine lauroyl. Also, the fatty acids useful according to the invention can be used in the form of their pharmacologically acceptable salts, such as alkali metal salts. Useful examples of such salts include the sodium and lithium salts.

The compounds according to the invention can be used singly or in mixtures. For example, it is preferred that from 1 to 6 compounds, especially from 1 to 4 compounds, be administered at one time.

The results of testing reflecting the usefulness of monoglyceride ethers and lysophosphatidylcholine derivatives are shown in the following Tables 7–10.

TABLE 7

Inactivation of vesicular stomatitis virus by monoglyceride ethers in human plasma[1]

| Monoglyceride Ether | Concentration (Mm) | Sodium Taurocholate (10 mM) | Reduction in VSV Titer ($\text{Log}_{10}$) |
|---|---|---|---|
| 1-O-Decyl-sn-glycerol[3] | 5 | + | 0 |
| 1-O-Octyl-sn-glycerol[2] | 10 | − | ≧4.0 |
|  | 10 | − | 2.0 |
| 1-O-Octyl-sn-glycerol | 15 | − | ≧4.0 |
| 1-O-Octyl-sn-glycerol | 5 | + | ≧4.0 |
|  | 10 | − | 1.3 |
|  | 15 | − | ≧4.0 |
| 1-O-Oleyl-sn-glycerol[4] | 5 | − | 0 |
|  | 10 | − | 0 |
|  | 15 | − | 0 |

[1] Incubations were done at 37° for 30 minutes.
[2] 8 carbon ether.
[3] 10 carbon ether.
[4] 18 carbon ether.

TABLE 8

| The antiviral activity of monoglyceride esters and ethers is additive[1] | | | | | | |
|---|---|---|---|---|---|---|
| Ether Concn. | | Ester Concn. | | Sodium Concn. | | Reduction in VSV |
| (Carbons) | (Mm) | (Carbons) | (Mm) | Taurocholate | (Mm) | Titer ($\log_{10}$) |
| 8 | 5 | 8 | 5 | − | — | 0 |
| 8 | 7.5 | 8 | 7.5 | − | — | 3.7 |
| 8 | 5 | 8 | 5 | + | 5 | ≧4.0 |
| 8 | 2.5 | 8 | 2.5 | + | 10 | ≧4.0 |
| 10 | 5 | 10 | 5 | − | — | 2.0 |
| 10 | 7.5 | 10 | 7.5 | − | — | 1.8 |
| 10 | 5 | 10 | 5 | + | 5 | ≧4.0 |
| 10 | 2.5 | 10 | 2.5 | + | 10 | ≧4.0 |
| 8 | 2.5 | 8 | 2.5 | − | — | 1.3 |
| 10 | 2.5 | 10 | 2.5 | | | |
| 8 | 2.5 | 8 | 2.5 | + | 5 | ≧4.0 |
| 10 | 2.5 | 10 | 2.5 | | | |

[1]Incubated at 37° for 30 minutes in human plasma.

TABLE 9

| Time course of VSV inactivation at 37° in human plasma with 15 Mm 1-O-octyl-sn-glycerol | |
|---|---|
| Incubation Time (min.) | Reduction in VSV Titer ($\log_{10}$) |
| 2.5 | 0 |
| 5 | ≧4.0 |
| 10 | ≧4.0 |
| 15 | ≧4.0 |
| 30 | ≧4.0 |

The 8 carbon and 10 carbon monoglyceride ethers are just as effective as the naturally occurring esters, and, in fact, the 8 carbon derivative appears to be somewhat more antiviral than the 8 carbon ester. The 18 carbon ether (Table 7) showed the same lack of antiviral activity as the ester in human plasma.

| Antiviral Activity of Lysophosphatidylcholine Derivatives | | | |
|---|---|---|---|
| Lipid | Conc (mM) | Sodium Taurocholate (10 mM) | $\log_{10}$ Reduction in VSV Titer |
| L-α-Lysophosphatidylcholine caproyl (8C) | 5 | + | 0 |
| | 5 | − | 0 |
| | 10 | + | 0 |
| | 10 | − | 0 |
| | 15 | + | 1.0 |
| | 15 | − | 0 |
| L-α-Lysophosphatidylcholine decanoyl (10C) | 5 | + | 1.7 |
| | 5 | − | 1.7 |
| | 10 | + | 1.7 |
| | 10 | − | 1.0 |
| L-α-Lysophosphatidylcholine lauroyl (12C) | 5 | + | 1.7 |
| | 5 | − | 1.2 |
| | 10 | + | 2.0 |
| | 10 | − | 2.0 |

The compounds employed as antimicrobials in the process of the invention may be prepared in-situ from inactive precursors. For example, inactive (as antimicrobials) lipid precursors are applied to the contact lens as a disinfectant. The inactive precursor, in the presence of the microbial is activated. For example, extra-cellular enzymes secreted by the microbe, function to activate the precursor.

More specifically, microbes such as, for example, *Pseudomonos aeruginosa*, secretes an extracellular lipase or phospholipase. The lipase will break an ester linkage in an inactive precursor molecule, leaving an active molecule remaining. The active molecule will be a fatty acid attached to a glycerol backbone by an ether linkage. Ethers are not cleaved by lipases. What we envision is that the inactive precursor will, for example, be a glycerol backbone with two fatty acids attached (a diglyceride). Diglycerides are not antimicrobial. One fatty acid will be attached by an ester linkage and the other by an ether linkage. The lipase will cleave the ester bond producing an active monoglyceride ether and a free fatty acid. The fatty acid released can be antimicrobial, or not, depending upon the design of the precursor.

As is set forth herein, the compounds of the invention have antimicrobial, especially antiviral and/or antibacterial, activity. Microorganisms that can be killed according to the invention include, but are not limited to, the following fungi, yeast, bacteria and viruses:

| | |
|---|---|
| | Fungi |
| Ringworm: | Dermatophytes |
| | Black piedra |
| | White piedra |
| | Tines nigra |
| | Tines versicolor |
| | Yeast |
| Yeast: | Candida albicans |
| | Viruses |
| Togaviridae family: | |
| Alphavirus (arbovirus group A) | mosquito-borne viruses |
| Flavivirus (arbovirus group B) | mosquito-borne viruses |
| | tick-borne viruses |
| Rubivirus | Rybella virus |
| Pestivirus | viruses of cattle and pigs |
| Orthomyxoviridae: | Influenza virus A |
| | Influenza virus B |
| | Influenza virus C |
| Paramyxoviridae: | Parainfluenza virus |
| | Mumps virus |
| | Newcastle disease virus |
| | Viruses of rinderpest and canine distemper virus |
| | respiratory syncytial virus |

| | |
|---|---|
| Retroviridae: | rabies viruses<br>sarcoma and leukemia viruses<br>visna virus<br>human immuno deficiency<br>viruses (AIDS)<br>human lymphotropic viruses<br>Types 1 and 2 |
| Herpesviridae: | Herpes simplex types 1<br>and 2<br>varicella zoster<br>cytomegalovirus<br>Epstein-Barr virus<br>All other members of<br>this group |
| Bacteria | |
| | Escherichia coli<br>Pseudomonas aeruginosa<br>Staphylococcus aureus |

The disinfectant compositions of the invention may be prepared by formulation of a mixture containing from about 10 µg/ml to 1000 mg/ml of the fatty acid or monoglyceride thereof (active ingredient).

The components of the formulations may also optionally include water-soluble polymers, inorganic electrolytes, and other small molecular weight substances to obtain desired characteristics. Water-soluble polymers may be added as supplementary wetting agents, film-forming agents, and viscosity modifiers. Some of the wetting agents possess both film-forming and viscosity modifying properties. Those agents possessing wetting and film-forming properties may be elected from, but are not limited to, nonionic polymeric surfactants used at concentrations ranging from 0.02% to 4.5% by weight, including poloxamers such as those manufactured by the BASF Wyandotte Corporation under the trademark Pluronic®, e.g. grade F68, or polyoxyethylene sorbitan esters such as those manufactured by ICI Americas, Inc., under the trademark Tween®, e.g. grade 80. Other agents possess viscosity modifying properties in addition to wetting and film-forming properties and these agents may be used to form part of the present invention. The latter agents include, but are not limited to substituted cellulose ethers such as hydroxypropylmethyl cellulose manufactured by Dow Chemical Company under the trade name Methocedor® or hydroxyethyl cellulose manufactured by Hercules Powder Co. under the name of Natrosol® 25OM and used in amounts from 0.1% to 0.5% by weight, povidone used at 0.1–5% by weight and manufactured by GAF Chemicals Corporation under the trade name PVP K30 and acrylic copolymers used from 0.1% to 0.5% by weight and manufactured by Th. Goldschmidt AG. under the trade name Merquat®.

The following preparations and examples describe the manner and process of making and using the invention and set forth the best mode contemplated by the inventors for carrying out the invention but are not to be construed as limiting. The active ingredient used in each example is, for illustrative purposes, capric acid. However, any of the fatty acids or monoglycerides thereof named above can be substituted. Lipids can be added to all 10 examples for antiviral, antimicrobial activity and eliminates any antibiotic resistant strains.

EXAMPLE 1

Contact Lens Disenfecting Solution

| | |
|---|---|
| Active Ingredient | 0.001% |
| Sodium chloride | 0.78% |
| Tetrasodium edetate | 0.08% |
| Boric acid | 0.35% |
| Sodium borate | 0.02% |
| Purified water | q.s. |
| pH | 6.0–8.0 |

The solution will disinfect a contact lens by soaking the lens for a period of from 0.5 to 12 hours at room temperature.

EXAMPLE 2

Contact Saline/Contact Lens Rinsing, Soaking, and Disinfecting Solution

| | |
|---|---|
| Active Ingredient | 0.001% |
| Sodium chloride | 0.78% |
| Tetrasodium edetate | 0.08% |
| Boric acid | 0.35% |
| Sodium borate | 0.02% |
| Purified water | q.s. |
| pH | 6.0–8.0 |
| Potassium chloride | 0.6% |

EXAMPLE 3

Contact Lens Disinfecting, Wetting, Soaking, and Reconditioning Solution

| | |
|---|---|
| Active Ingredient | 0.001% |
| Tetrasodium edetate | 0.12% |
| Hydroxypropylmethyl cellulose % | 0.40% |
| Acrylic polymer | 0.50% |
| Sodium chloride | 0.8% |
| Boric acid | 0.35% |
| Sodium borate | 0.02% |
| Tween 80 | 0.02% |
| Purified water | q.s. |
| pH | 7.0–8.0 |

EXAMPLE 4

Contacting Lens Cleaning Solution

| | |
|---|---|
| Active Ingredient | 0.001% |
| Tetrasodium edetate | 0.12% |
| Pluronic F68 | 4.5% |
| Boric acid | 0.35% |
| Sodium borate | 0.02% |
| Purified water | q.s. |

EXAMPLE 5

Lens Cushioning Solution

| | |
|---|---|
| Active Ingredient | 0.001% |
| Tetrasodium edetate | 0.12% |
| Hydroxypropylmethyl cellulose % | 0.15% |

-continued

| | |
|---|---|
| Povidone | 0.50% |
| Sodium chloride | 0.85% |
| Boric acid | 0.35% |
| Sodium borate | 0.02% |
| Purified water | q.s. |
| pH | 7.0–8.0 |

This antimicrobial agent can also be added to tear substitutes used in the treatment of the dry eye syndrome comprising the antimicrobial formulation of the present invention combined with additional salts to form a physiological balanced salt solution and additional wetting agents, film forming agents, and viscosity modifying agents such as those previously described.

In addition, the antimicrobial composition of the present invention can be used as a vehicle for preserving the active agents, e.g. drugs used in ophthalmic medicaments. The antimicrobial composition of the present invention can also be used to preserve ophthalmic suspensions and ointments.

The following drugs are examples of ophthalmic drugs and are not intended to limit the scope of the invention. The medicaments are selected on the basis of diagnosis and indicated treatment for patients; dexamethasone for ocular inflammation, pilocarpine hydrochloride or beta-blockers for elevated intraocular pressure, and hydrochloric salts of ephedrine, phenylephrine, naphazoline, and tetrahydrozoline for injected eyes. For the treatment of ocular allergic reaction, antihistamines or mast-cell stabilizers could be included among the active ingredient preserved formulae.

EXAMPLE 6

Artificial Tear Formulation

| | |
|---|---|
| Active Ingredient | 0.001% |
| Tetrasodium edetate | 0.12% |
| Hydroxypropylmethyl cellulose % | 0.20% |
| Sodium chloride | 0.77% |
| Potassium chloride | 0.11% |
| Calcium chloride dihydrate | 0.08% |
| Magnesium chloride 7H$_2$O | 0.02% |
| Boric acid | 0.35% |
| Sodium borate | 0.02% |
| Purified water | q.s. |
| Ph | 7.5 |

EXAMPLE 7

Anti-inflammatory Emulsion

| | |
|---|---|
| Dexamethasone | 0.05% |
| Active Ingredient | 0.0001% |
| Tetrasodium edetate | 0.12% |
| Substituted cellulose ether | 0.40% |
| Sodium chloride | 0.8% |
| Boric acid | 0.35% |
| Sodium borate | 0.02% |
| Tween 80 | 0.02% |
| Purified water | q.s. |
| Ph | 7.2 |

EXAMPLE 8

Ocular Hypotensive Preparation

| | |
|---|---|
| Pilocarpine Hcl | 0.5% |
| Active Ingredient | 0.001% |
| Tetrasodium edetate | 0.12% |
| Substituted cellulose ether | 0.40% |
| Sodium Chloride | 0.8% |
| Boric acid | 0.35% |
| Sodium borate | 0.02% |
| Purified water | 0.02% |
| Ph | 6.5 |

EXAMPLE 9

Vaso-constrictor containing preparation

| | |
|---|---|
| Phenylepohrine HCl | 0.1% |
| Active Ingredient | 0.001% |
| Tetrasodium edetate | 0.12% |
| Substituted cellulose ether | 0.20% |
| Sodium chloride | 0.8% |
| Boric acid | 0.35% |
| Sodium borate | 0.02% |
| Purified water | q.s |
| pH | 7.4 |

EXAMPLE 10

Anti-viral Ointment

| | |
|---|---|
| Acyclovir | 3.0% |
| Active Ingredient | 0.001% |
| Tetrasodium edetate | 0.12% |
| Boric acid | 0.35% |
| Sodium borate | 0.02% |
| Propylene glycol | 4.5 |
| White soft paraffin wax | 38% |
| Paraffin oil | q.s. |

What is claimed is:

1. A process for disinfecting a contact lens, which comprises; applying to the lens an effective antimicrobial amount of a compound selected from the group consisting of $C_6$–$C_{14}$ fatty acids, salts and monoglycerides thereof, $C_6$–$C_{14}$ fatty alcohols, $C_{16}$–$C_{20}$ mono-or polyunsaturated fatty acids, salts and monoglycerides thereof, $C_{16}$–$C_{20}$ mono- or polyunsaturated fatty alcohols, and ether and lysophosphatidylcholine derivatives of $C_4$–$C_{22}$ fatty acids.

2. The process of claim 1 wherein the contact lens is a soft contact lens.

3. The process of claim 1 wherein the compound selected is in an ophthalmically acceptable carrier.

4. The process of claim 3 wherein the effective antimicrobial amount is within the range of from about 10 µg/ml to 1000 mg/ml of the carrier.

5. The process of claim 3 wherein applying is by soaking.

6. The process of claim 1 wherein the compound selected is a fatty acid with from 4 to 14 carbon atoms.

7. The process of claim 1 wherein the compound selected is a saturated fatty alcohol having 6 to 14 carbon atoms.

8. The process of claim 1 wherein the compound selected is a fatty acid monoglyceride having 7 to 12 carbon atoms.

9. The process of claim 1 wherein the compound selected is an ether derivative of a fatty acid having 4 to 22 carbon atoms.

10. The process of claim 1 wherein the compound selected is a lysophosphatidylcholine derivative of a fatty acid having 4 to 22 carbon atoms.

11. An artificial tear composition which comprises; an effective antimicrobial amount of a compound selected from the group consisting of $C_6$–$C_{14}$ fatty acids, salts and monoglycerides thereof, $C_6$–$C_{14}$ fatty alcohols, $C_{16}$–$2_{20}$ mono or polyunsaturated fatty acids, salts and monoglycerides thereof, $C_{16}$–$C_{20}$ mono - or polyunsaturated fatty alcohols, and either and lysophosphatidylcholine derivatives of $C_4$–$C_{22}$ fatty acids; water, salts to form a physiological balanced salt solution, wetting agents, film forming agents and viscosity modifying agents.

12. The composition of claim 11 which further comprises;

tetrasodium edetate;

hydroxyproplymethyl cellulose;

sodium chloride;

potassium chloride;

calcium chloride dihydrate;

magnesium chloride $7H_2O$;

boric acid;

sodium borate; and purified water.

* * * * *